United States Patent
Kawasaki et al.

(10) Patent No.: US 7,353,054 B2
(45) Date of Patent: Apr. 1, 2008

(54) OPTICAL MEASUREMENT APPARATUS FOR LIVING BODY

(75) Inventors: Shingo Kawasaki, Matsudo (JP); Noriyoshi Ichikawa, Moriya (JP); Fumio Kawaguchi, Hinode-machi (JP); Naoki Tanaka, Saitama (JP); Hideo Kawaguchi, Saitama (JP); Masahiko Mikuni, Maebashi (JP); Masato Fukuda, Saitama (JP)

(73) Assignees: Hitachi Medical Corporation, Tokyo (JP); Hitachi, Ltd., Tokyo (JP); National University Corporation Gunma University, Maebashi-Shi (JP)

( * ) Notice: Subject to any disclaimer, the term of this patent is extended or adjusted under 35 U.S.C. 154(b) by 8 days.

(21) Appl. No.: 10/571,430

(22) PCT Filed: Sep. 9, 2004

(86) PCT No.: PCT/JP2004/013121

§ 371 (c)(1),
(2), (4) Date: Mar. 10, 2006

(87) PCT Pub. No.: WO2005/025421

PCT Pub. Date: Mar. 24, 2005

(65) Prior Publication Data

US 2007/0055118 A1    Mar. 8, 2007

(30) Foreign Application Priority Data

Sep. 11, 2003 (JP) .............................. 2003-319502

(51) Int. Cl.
A61B 5/00   (2006.01)

(52) U.S. Cl. ...................... 600/310; 600/300

(58) Field of Classification Search ............ 600/300, 600/322, 323, 328; 128/923
See application file for complete search history.

(56) References Cited

U.S. PATENT DOCUMENTS

| | | | | |
|---|---|---|---|---|
| 5,551,436 A | * | 9/1996 | Yago | 600/483 |
| 5,746,204 A | * | 5/1998 | Schauss | 600/300 |
| 6,059,724 A | * | 5/2000 | Campell et al. | 600/300 |
| 6,063,026 A | * | 5/2000 | Schauss et al. | 600/300 |
| 6,240,309 B1 | * | 5/2001 | Yamashita et al. | 600/407 |

(Continued)

FOREIGN PATENT DOCUMENTS

JP       09-149894       6/1997

(Continued)

*Primary Examiner*—Eric Winakur
*Assistant Examiner*—Etsub D Berhanu
(74) *Attorney, Agent, or Firm*—Antonelli, Terry, Stout & Kraus, LLP.

(57) ABSTRACT

An apparatus which can objectively assess and display to what extent and to which disease the subject belongs based on the signals of changes in hemoglobin amount measured by the optical measurement apparatus is provided. The disease assessment apparatus comprises the feature extraction unit 15 for extracting features of the hemoglobin waveform, the feature analysis unit 16 and the storage unit 12 for storing features by each disease as database. The disease is assessed by extracting various kinds of feature amounts from the hemoglobin signals of the subject measured by the optical measurement apparatus in the feature extraction unit 15 and by applying multivariate analysis of similarities between feature amounts extracted and feature amounts stored by disease in the storage unit 12. Results of assessment are shown as scores expressing similarity with each disease group in a bar graph.

14 Claims, 12 Drawing Sheets

U.S. PATENT DOCUMENTS 7,186,217 B2 * 3/2007 Kawasaki .................. 600/300

FOREIGN PATENT DOCUMENTS

| JP | 10-216113 | 8/1998 |
| JP | 2000-300569 | 10/2000 |
| JP | 2001-079008 | 3/2001 |
| JP | 2001-212114 | 8/2001 |
| JP | 2002-136505 | 5/2002 |
| JP | 2003-275191 | 9/2003 |

* cited by examiner

Fig.3
Normal Subject
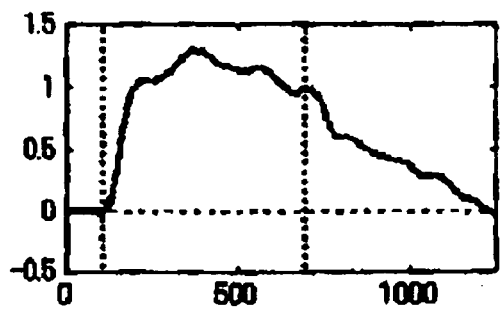
Schizophrenia
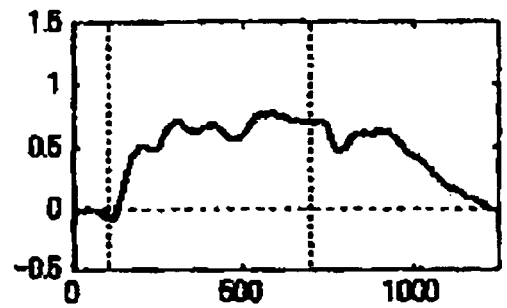
Depression
Manic-depressive Psychosis
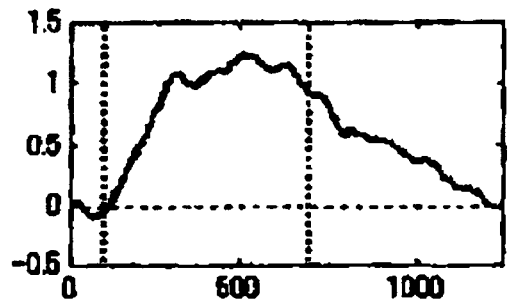

Fig.5
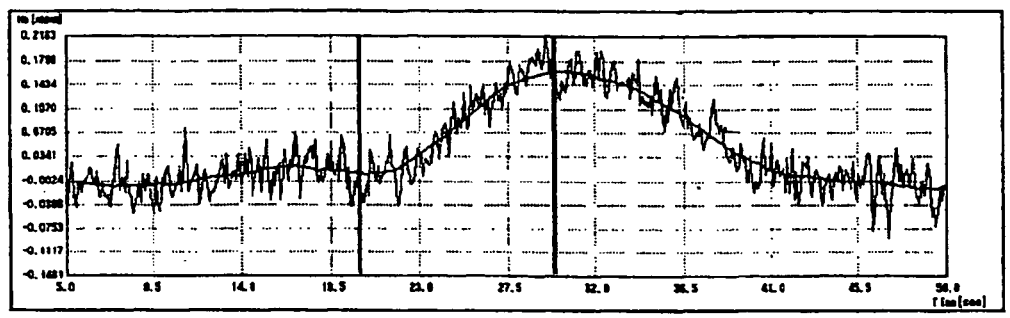
(a)
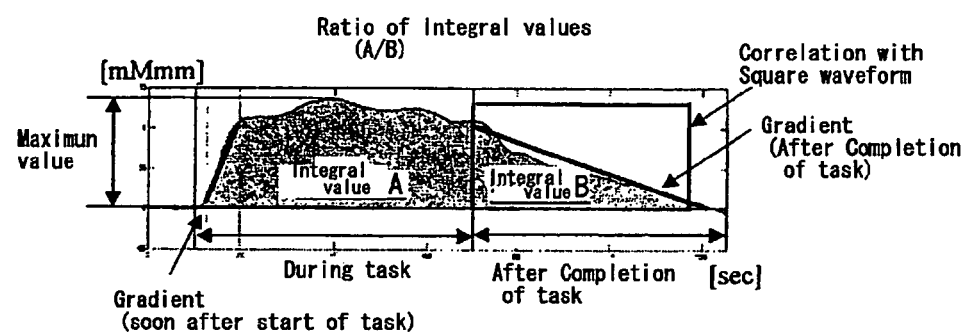
(b)

Fig.6

Data in Groups

| Group NC | | Group S | | Group D | |
|---|---|---|---|---|---|
| Maximum value | Gradient | Maximum value | Gradient | Maximum value | Gradient |
| 7 | 8 | 107 | 58 | 120 | 10 |
| 30 | 28 | 130 | 78 | 130 | 40 |
| 60 | 29 | 160 | 79 | 140 | 30 |
| 28 | 55 | 128 | 105 | 150 | 24 |
| 57 | 60 | 157 | 110 | 155 | 30 |
| 77 | 62 | 177 | 112 | 145 | 37 |
| 69 | 77 | 169 | 127 | 130 | 35 |
| 55 | 94 | 155 | 144 | 200 | 15 |
| 96 | 93 | 196 | 143 | 190 | 23 |
| 111 | 134 | 211 | 184 | 180 | 34 |

Fig.10
(a) NC22(Normal)    S06 (Schizophrenia)    D05 (Depression)
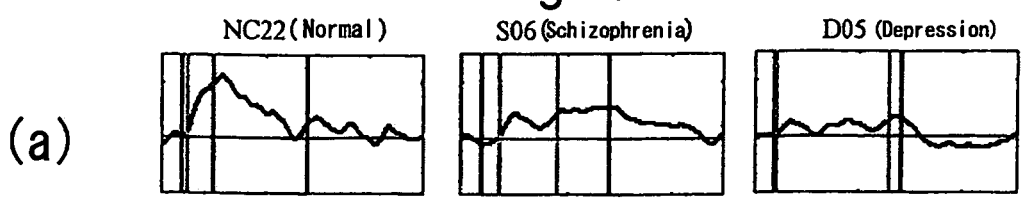
Mahalanobis distance to each disease group
(b)
| Object | Distance to NC Dnc | Distance to S Ds | Distance to D Dd | Assessment |
|---|---|---|---|---|
| NC22 | 3 | 8 | 25 | NC |
| S06 | 3 | 2 | 28 | S |
| D05 | 5 | 7 | 2 | D |
(c)
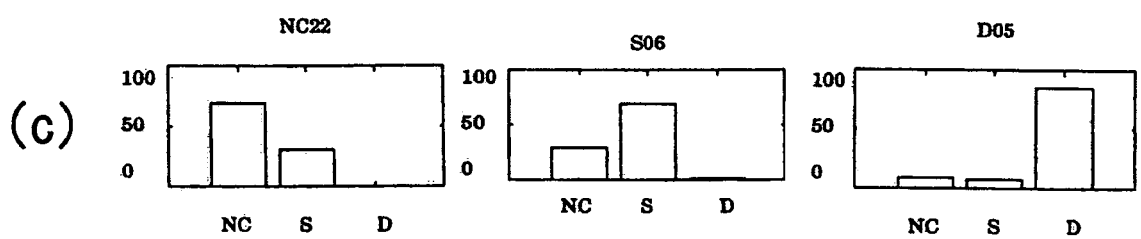

OPTICAL MEASUREMENT APPARATUS FOR LIVING BODY

FIELD OF THE INVENTION

The present invention relates to an optical measurement apparatus for living body (hereinafter referred to "optical measurement apparatus"), which measures blood circulation, blood flow and change of the hemoglobin amount inside the living body by irradiating near infrared light onto the living body and by measuring a light that passes through or reflects inside the living body. Particularly, it relates to an apparatus which assesses various types of diseases by using the results measured by the optical measurement apparatus.

BACKGROUND OF THE INVENTION

The optical measurement apparatus can simply measure blood circulation, blood flow and change of the hemoglobin amount inside the living body under with less constraint and without damage to the subjects. Because of recent success in visualizing measurement data by using a multichannel apparatus, clinical application of this apparatus is highly expected.

It has been reported that clinical applications of the optical measurement apparatus include diagnosis of epilepsy, cerebral ischemia and other diseases and investigation of language function. Non-patent documents 1 and 2 listed below report that the biological optical measurement founds abnormality in the pattern of change of the hemoglobin amount in the frontal lobe of psychiatric-patients such as depression and schizophrenia. Concretely, the maximum value of a time waveform of hemoglobin is large, small and medium in normal subjects, depressive patients and schizophrenic patients, respectively. These reports suggest potential of using the time waveform of hemoglobin in the diagnosis of psychosis. However, because the time waveform of hemoglobin is obtained as data by each of channels when a multi-channel optical measurement apparatus is used, it is not easy to do accurate diagnosis by comparing these multiple waveforms.

Non-patent document 1: "Significance of multi-channel near infrared spectroscopy (NIR) measurement in psychiatry" Masato Fukuda, et al. "Brain Science and Mental Disorders", Volume 14, No. 2 (Special Volume), Shinkoh-Igaku Shuppan Co., Ltd. Non-patent document 2: "Mind viewed with light (HIKARI DE MIRU KOKORO)" Masato Fukuda, et al. "Kokoro and Shakai (Mind and Society)", Volume 34, No. 1 (Special Volume), Japanese Association of Mentaly Health (Nippon Seisin-eisei kai)

The applicant of this invention has also proposed a optical measurement apparatus equipped with functions to extract features from the waveforms of change in the hemoglobin amount, convert them into numerical data and display them each of disease (Japanese Patent Application No. 2002-85350). This optical measurement apparatus can, by comparing the feature amount displayed for each disease and that measured for the subjects, estimate the degree of disease with respect to said measured feature amount.

However, for accurate diagnosis of disease, particularly psychopathic disease, a comprehensive diagnosis based on the multiple features rather than a single feature is required. When said optical measurement apparatus is used, a doctor and/or operator is required to perform a comprehensive diagnosis based on the individual feature amount.

DISCLOSURE OF THE INVENTION

Problems to be Solved by the Invention

Accordingly, the object of this invention therefore is to provide an apparatus, which can analyze various feature amounts extracted from hemoglobin signals, which are results of measurement, obtained by the optical measurement apparatus, and display for determination objectively to them to what disease and in what extent each signal is attributed.

Means for Solving the Problems

In order to solve the afore-mentioned problems, the present invention provides an optical measurement apparatus for a living body comprising a light source for generating a light irradiated to an object to be examined, a light measurement means for detecting a light transmitted inside the object and generating hemoglobin signals corresponding to hemoglobin density change in the object, an assessing means that analyzes feature amounts of the hemoglobin signals and estimates a disease of the object from the analyzed feature amount, and a display means for displaying disease information of the object.

In the optical measurement apparatus of the present invention, preferably, the assessing means comprises a means for extracting various feature amounts from the hemoglobin signals, a storing means for storing the feature amounts of each disease into database, an analyzing means for analyzing the feature amounts extracted by the extracting means and for assessing its similarity with the feature amount of each disease stored in the storing means, and a quantifying means for quantifying the similarity assessed by the analyzing means.

In the optical measurement apparatus of this invention, preferably, the analyzing means calculates similarity between various feature amounts extracted by the extracting means and feature amount data of each disease stored in the storing means by multivariate analysis. As one of the multivariate analysis methods, the analyzing means can obtain similarity by calculating the Mahalanobis' distance between the feature amounts of the object and (the gravity center of) the feature amounts of each disease. Mahalanobis' distance is often referred as Mahalanobis' generalized distance but is a synonym for the latter. The Mahalanobis' distance enables an accurate assessment not affected by potential scattering of variance of each disease data.

In the optical measurement apparatus of this invention, preferably, the extracting means extracts various feature amounts from the patterns of change in the hemoglobin amount while the task is loaded. Concretely, various feature amounts include at least one of such parameters as a gradient of the graph immediately after the initiation of the task, a gradient of the graph after the completion of the task, an integral value A during the task, an integral value B after the completion of the task, a ratio of integral values (A/B), a maximum value and a correlation value between square waveform and waveform after the completion of the task.

In the disease assessment apparatus of this invention, preferably, the displaying means displays similarity graphically.

According to this invention, by estimating the results of optical measurement comprehensively and displaying them in a form to be understandable at once, it becomes possible to assess disease easily and objectively.

Further, in the optical measurement apparatus of the invention, the extracting means uses a mean value of values obtained by multiple measurements as the hemoglobin signals. This improves reliability of the assessed result.

In an embodiment of the optical measurement apparatus of the invention, the storing means includes database of feature amounts for, at least, normal subject group, schizophrenia group and depression group.

The optical measurement of the invention may be equipped with a storing means for storing the assessed results for each subject together with its measurement data obtained by optical measurement for a living body and image data as a combined data.

Further, in the optical measurement apparatus of this invention, the analyzing means can select a data of a subject of assessment whose similarity with a particular disease is within a predetermined threshold value and stores it to data of said particular disease in the storage unit.

According to this optical measurement apparatus, since data of the subjects of assessment can be added to the database stored in the storage unit, it is possible to enlarge the size of the database and improve accuracy of assessment.

The optical measurement apparatus, preferably, is equipped with an input means for inputting direction of assessment by the assessing means, preparation of reports, update of database and displaying by the display means.

The present invention further provides a method of estimating disease of an object using hemoglobin signals of the object measured by optical measurement comprising the steps of; producing a database of feature amounts of a plurality of disease groups by measuring hemoglobin signals by optical measurement for a plurality of subjects whose diagnosis of disease among the disease groups has been established, extracting a plurality of feature amounts from the hemoglobin signal of each subject and storing the feature amounts as database, and assessing disease of an object to be examined by extracting a plurality of feature amounts from a hemoglobin signal measured by optical measurement for the object to be examined, calculating a similarity of the extracted feature amounts with the data for each disease in the database and determining a disease having a highest similarity as a disease of the object to be examined.

The method of estimating disease of the invention preferably includes further the steps of extracting principal component waveform by conducting principal component analysis for hemoglobin signals of a plurality of subject each whose diagnosis of disease has been established, extracting feature amounts from the principal component waveform of each subject, and storing the extracted feature amount as data of the disease of the subject.

PREFERRED EMBODIMENT OF THE INVENTION

Embodiments of this invention are explained below with reference to the attached drawings.

FIG. 1 is a block diagram illustrating the configuration of major components in the disease assessment apparatus of this invention. The disease assessment apparatus 10 comprises mainly an operation unit 11, which inputs signals of changes in the hemoglobin amount (hemoglobin-amount-change signals) from the optical measurement apparatus 20 and carries out operations including feature extraction and feature analysis, a storage unit 12, which stores specified features of each disease in database, an input unit 13, which inputs instructions necessary for processing at the operation unit 11, and a display unit 14, which displays results of analysis. The operation unit 11 further comprises a feature extraction unit 15, which extracts specified features from the pattern of changes in the hemoglobin-amount-change signals, and a feature analysis unit 16, which calculates similarity by comparing features extracted at the feature extraction unit 15 with the features of each disease. Further, the storage unit 12 stores the results obtained by analyzing feature amounts of multiple patients whose diagnosis has been established by other diagnosing method as a data of each disease group. Although not illustrated, the disease assessment apparatus is equipped with a main control unit, which controls the operation unit 11, storage unit 12, input unit 13 and display unit 14.

This disease assessment apparatus 10 extracts specified features from the hemoglobin-amount-change signals to be sent from the optical measurement apparatus 20 at the feature extracting unit 15, calculates similarity between extracted features and the features of each disease group stored in the storage unit 12 at the feature analysis unit 16, judges the subject as having a disease of the group, the similarity with which is highest, and displays the results in the display unit 14. This disease assessment apparatus 10 may process the hemoglobin-amount-change signals sent from the optical measurement apparatus 20 in real time and display the result of assessment. Alternately the disease assessment apparatus 10 may store data measured by the optical measurement apparatus 20 in the temporary data storage unit, read the data for each patient out of the storage unit, as required, and judge the disease. In this case, the storage unit for storing the measurement data temporarily maybe installed either at the side of the optical measurement apparatus 20 or at the side of the disease assessment apparatus 10. The disease assessment apparatus of this invention may receive the measurement data from the optical measurement apparatus 10 installed at a remote place through a communication means and process them.

Individual components of the optical measurement apparatus 20 and the disease assessment apparatus 10 and their actions are explained below.

The optical measurement apparatus 20 is an apparatus, which irradiates near infrared light inside the living body, detects a light that passes through the living body or reflected near the surface of the living body (hereinafter, referred to transmitted light) and generates electric signals with an intensity corresponding to that of light. In this embodiment, the case in which a multi-channel optical measurement apparatus to measure transmitted lights from multiple positions by irradiating a light modulated with different frequencies onto multiple positions of the living body (e.g. head) is used is explained.

This optical measurement apparatus comprises, as shown in FIG. 2, a light source unit 21, which irradiates near infrared light, an optical measurement unit 26, which measures transmitted light and converts it into electric signals, and a control unit 30, which controls the operation of the light source unit 21 and an optical measurement unit 26. The light source unit 21, further comprises a semiconductor laser, which radiates light with a specified wavelength and multiple light modules 23 equipped with a modulator for modulating light generated by the semiconductor laser 22 with multiple different frequencies, wherein output light of each light module 23 is irradiated through each light fiber 24 from specified measurement regions, such as multiple positions of the head. An optical measurement unit 26 comprises a photoelectric conversion element 27, such as photodiode, which converts transmitted light guided through an optic fiber 25 from multiple measurement positions in the measurement region into the quantity of electricity corresponding to the quantity of light, a lock-in amplifier 28, which inputs electric signals from the photoelectric conversion element 27 and selectively detects modulated signals corresponding to the light irradiation position and an A/D converter 29, which converts the outputted signals from the lock-in amplifier 28 into digital signals.

Further, the light source unit 21 is configured generally to generate the light of two different wavelengths, for example 780 nm and 830 nm, in correspondence to two different objects of measurement, such as oxygenated hemoglobin and de-oxygenated hemoglobin. The light of two different wavelengths is synthesized and irradiated from a single irradiating position. The lock-in amplifier 28 selectively detects the light irradiating position and modulated signals corresponding to these two different wavelengths. Consequently, hemoglobin-amount-change signals of a channel number twice a number of positions (measuring positions) between the light irradiating and detecting positions are obtained.

A control unit 30 comprises a signal processing unit 31, an input/output unit 32 and a storage unit 33. The signal processing unit 31 processes hemoglobin-amount-change signals which has been converted to digital signals, and produces a graph showing changes in the oxygenated hemoglobin concentration, changes in the deoxygenated hemoglobin concentration and a total hemoglobin concentration by channel and the images in which they are plotted on a two-dimensional image for the object to be examined. The input/output unit 32 displays the results of processing at the signal processing unit 31 and various directions necessary for the operation of the apparatus are input using the input/output unit 32. The storage unit 33 stores data necessary for the processing at the signal processing unit 31 and the results of processing.

In the optical measurement apparatus 20, hemoglobin-amount-change signals are measured under a specified task loaded to the subject as a differential signal from the value before loading the task. Such tasks as language stimulation load, visual stimulation and pain-producing stimulation are generally used. In assessment of psychiatry diseases, "verbal fluency task" is applied, in which the subject is asked to recall as many words starting with "ko" (phonetic) as possible.

As reported in the aforementioned non-patent documents 1 and 2, etc., the pattern of changes in the hemoglobin amount measured under such task is known to have different features according to disease. FIG. 3 shows a pattern of changes in the hemoglobin amount for each psychiatry disease, in which the vertical and horizontal axes show the intensity of signal and the time, respectively, while the space between two vertical dotted lines shows the length of time while the task is loaded. The pattern shown in the figure is one in which the feature is most prominently manifested among multi-channel signals. As illustrated in the figure, the signal intensity changes dramatically in normal subjects when the task is loaded and begins to decline simply when the task is withdrawn. The signal value in schizophrenic patients shows no dramatic change unlike normal subjects, and re-rises even after the completion of the task. While the signal value in depressive patients shows small changes under the task, in the patients with manic-depressive psychosis, the signal value changes dramatically under the task is loaded, but reaches its peak with some delay after loading the task.

Database stored in the storage unit 12 in the disease assessment apparatus 10 of this embodiment contains features of the patterns of changes in the hemoglobin amount extracted for each disease. It can be produced by using, for example, the technology described in the Patent Application No. 2002-85350 filed by this applicant. In the disease assessment apparatus 10 of this embodiment, the feature extraction unit 15 performs this function. The procedure to produce the database is shown in FIG. 4.

Firstly, the signals of changes in the hemoglobin amounts of individual patients whose diagnosis has been established by other method are inputted (Step 401), and then by analyzing principal components of the hemoglobin-amount-change signals of each channel, a signal which most closely reflects the biological reaction is obtained (Step 402). The analysis of the principal components can use the value of a raw hemoglobin signal obtained by a single measurement, but preferably use the average of multiple values obtained by a plurality of measurements. The plurality of measurement values may be obtained by repetition of the measurement and loading of a task performed continuously or at regular intervals. When the measurement data for both oxygenated and de-oxygenated hemoglobin are available, the waveform of the principal component of each hemoglobin data may be calculated separately. In either case, filtration for removing noise, etc. prior to the principal component analysis is preferably performed.

Filtration can use HPF for removing low-frequency noise and LPF for removing high-frequency noise. It is possible to pre-set a cutoff frequency at an appropriate value and a window function as a filtration function, and allow users to change them freely as required. FIG. 5 (a) illustrates raw signals of changes in the hemoglobin amount after filtration.

The principal component analysis is a method to contract high-dimensional data to lower dimensional one with minimum loss. Here, the measurement data consisting of the intensity of hemoglobin signals with time and the number of channels as parameters are converted to data with a fewer number of channels by contracting the channel axis. The procedures of the principal component analysis of this invention are explained below.

Signals of changes in the regional cerebral blood volume (hemoglobin amount), X, measured by the biological optical measurement apparatus 20 are assumed to be given by the following matrix.

$$X = \begin{bmatrix} x_1(1) & x_1(2) & \cdots & x_1(N) \\ x_2(1) & x_2(2) & \cdots & x_2(N) \\ \vdots & \vdots & \ddots & \vdots \\ x_m(1) & x_m(2) & \cdots & x_m(N) \end{bmatrix} \quad (1)$$

Where, N is the number of measured data, while m is the number of measured channels. As the matrix $XX^T$ is symmetric, it can be diagonalized with orthogonal matrix, W, namely, If $$Y = WX \quad (2)$$

$$YY^T = \text{diag}[\lambda 1, \lambda 2, \ldots, \lambda m] \quad (3)$$

It is assumed that Diag represents an orthogonal matrix and that $\lambda 1, \lambda 2, \ldots, \lambda m$ represent eigenvalues in descending order. The i-th row vector, $y_i$, therefore, is linear independent from other row vector, $y_j$ (j≠i). Eeigenvalue is also called as proportion rate, and higher eigenvalue means higher proportion in Matrix X.

In this invention, a vector $y_j$ is called as a principal component of i-throw. If $x_j$ is measured data of the j-th channel, the principal component of i-th row can be obtained from equation (2) and expressed as follows;

$$y_i = \sum_{j=1}^{m} w_{ij} X_j \qquad (4)$$

Where the coefficient $w_{ij}$ is a signed-weight of each channel in the i-th principal component, and its absolute value corresponds to the existence frequency of the principal component waveform in each channel. The sign is attached so that positive sign shows changes in blood volume in positive reaction.

Multiple waveforms (component m) are thus obtained as principal component waveforms. In order to select the task-associated change in blood volume, the waveform with highest proportion rate $\lambda i$, highest average presence frequency $\Sigma w_{ij}$ and highest correlation with specified reference response waveform is selected from these multiple waveforms as a principal component waveform. The reference documents shown below report that the changes in blood volume associated with nerve activity in the cerebral cortex increase with some delay after the initiation and the completion of the task. In this embodiment, when the task-associated change in blood volume is selected from the principal component waveforms, a trapezoidal waveform that begins to increase a few seconds after initiating the task and begins to decrease a few seconds after completing the task is produced and established as a reference response waveform and the correlation with this is calculated.

"Non-invasive assessment of language dominance with near-infrared spectroscopic mapping" E. Watanabe, A. Maki, F. Kawaguchi, K. Takashiro, Y, Yamashita, H. Koizumi, & Y. Mayanagi, Neuroscience Letter, 256, 49/52(1998)

"Processing strategies for time-course data sets in functional MRI of the human brain" P. A. Bandettini, A. Jesmanowicz, G. Eric. J. Wong & S. Hyde, Magn. Reson. Med., 30, 161/173(1993)

After the principal component waveform is thus extracted, the features of the principal component waveform are extracted (Step 403). In order to improve accuracy of extraction of the feature amounts, baseline processing of the principal component waveform is preferably performed prior to the feature extraction. The baseline processing is to make the line connecting signal values before initiating the task and those after completing the task, as a baseline, coincide with the horizontal axis of the graph. Concretely, an approximate curve calculated for the principal component waveform is used as a baseline in the processing. The degree of the approximate curve calculation is set appropriately. Results of baseline processing (AFP) is expressed with the principal component waveform (PW) and approximate curve (PF) in a formula:

$$ABW = PW/PF.$$

Any feature is usable if the pattern can be numerically expressed. In this embodiment, as shown in FIG. 5, the gradient of a graph immediately after the initiation of the task, a graph after the completion of the task, the integral value A during the task, the integral value B after the completion of the task, the ratio of integral values (A/B), the maximum value and the value of correlation with square waveform after the completion of the task are extracted as the feature amounts. These feature amounts can be obtained automatically by scanning the graph along the axis of time. For example, the gradient of the graph immediately after the initiation of the task can be determined automatically based on the value at the point of pre-determined elapse of time after the initiation of the task. The value of correlation with the square wave of the waveform after completing the task is employed in order to reflect the feature that the changes in blood volume increase after completing the task in schizophrenic patients. The correlation coefficient $\rho$ between the principal component waveform graph, X(t) and the square wave, Y(t) is obtained with the following formula:

$$\rho = C_{x(t)y(t)} / \sigma_{x(t)} \sigma_{y(t)}$$

where $C_{x(t)y(t)}$: covariance, $\sigma_{x(t)}$: variance of x(t), $\sigma_{y(t)}$: variance of y(t)

Aforementioned steps from the extraction of the principal component waveforms to the extraction of the feature amounts are performed on the hemoglobin-amount-change signals obtained from multiple patients with different diseases. Seven-dimensional features thus obtained are grouped by disease and stored in the storage unit 12 (Step 404). In this embodiment, these seven-dimensional feature amounts are stored separately for normal control group (Group NC), schizophrenia group (Group S) and depressive group (Group D). As the disease assessment apparatus of this embodiment is on the assumption that the data of these groups have a normal distribution, the number of data needs to be high enough to be regarded as having a normal distribution. Concretely, assessment is substantially effective if the number of data exceeds 10.

An example of database is shown in FIG. 6, where only two of seven-dimensional feature amounts, the maximum value and the gradient of the graph after completing the task, are shown. Numbers in the vertical column represent the data numbers.

Next, the operation of the disease assessment apparatus with such database is explained below. FIG. 7 shows the operating procedures. First, optical measurement using the optical measurement apparatus 20 is applied to the subject to measure waveforms (Step 701). This measurement is conducted on the same conditions as those of the measurement performed for producing database for the disease assessment apparatus 10. Specifically, the same task is applied to the subject with the same interval of task so that the data is measured under loading the task.

FIG. 8 shows an example of hemoglobin-amount-change signals obtained by the optical measurement for each channel of the optical measurement apparatus. In the embodiment shown in FIG. 8, measured data is obtained on 12 channels for the right and left of temporal lobe respectively.

The disease assessment apparatus 10 put these measured data into the operation unit 11, calculates the principal component waveform on the feature extraction unit 15 (Step 702) and extracts the feature amounts of the principal component waveform (Step 703). These steps 702 and 703 are same with those for producing database, wherein the principal component analysis is performed to identify the principal component waveform that has the maximum number of features of the subject and is most closely associated with the task. Then, after baseline processing of thus identified principal component waveform, seven-dimensional feature amounts (the gradient of a graph immediately after the initiation of the task, the gradient of a graph after the completion of the task, the integral value A during the task, the integral value B after the completion of the task, the ratio of integral values (A/B), the maximum value and the correlation value with square waveform of the waveform after the completion of the task) are obtained.

Next, similarity between seven-dimensional feature amounts extracted for the subject 1 on the feature extraction unit 15 and the feature amount for each disease group stored in the storage unit 12 is calculated on the feature analysis unit 16 (Step 704). Calculation of similarity uses various distances used in the discriminant analysis of multivariate analysis, including Euclid distance, standardized Euclid distance, maximum distance and Mahalanobis distance. Although all of these distances are applicable in this invention, similarity evaluation using Mahalanobis distance is explained below.

If feature amounts for the subjects is expressed as C=(C1, C2, C3, ..., Ck)' (k=7) and mean vectors of the feature amount for the database on the j-th disease groups (a total 3 groups) as mj=(mj1, mj2, mj3, ..., mjk)' (k=7), the mahalanobis distance dj between center of gravity (mean value) of j-th disease group and the subjects is given by the following equation (5).

$$dj^2 = f(C) = (C-mj)' \Sigma^{-1} (C-mj) \quad (5)$$

($\Sigma$ is a variance covariance matrix (k*k dimension) of the database on the j-th disease group, while $\Sigma^{-1}$ represents its inverse matrix)

Consequently, the Mahalanobis distance to each disease group can be obtained by calculating mean vectors and a variance matrix of k coefficients of each group. Subjects are classified into the group, Mahalanobis distance to which is shortest. The discriminant analysis using this Mahalanobis distance may lead to more credible discrimination even the covariance matrix and the population variance among groups are not equal.

FIG. 9 is a graphical presentation of two-dimensional data of three groups (groups NC, S and D) shown in FIG. 6, where a feature amount (point P) of one subject is connected to the gravity center of each group by a straight line. The length of the straight line corresponds to the Euclidian distance from the subject. When the Mahalanobis distance of the gravity center of each group from the feature amounts of the subject is calculated using the equation (5), it becomes 3.53 for Group NC, 13.03 for Group S and 120.19 for Group D. When the Euclidian distance is used, the feature amount of a subject (point P) is closer to the gravity center of Group S than to Group NC. However, when the Mahalanobis distance is used, the subject is classified here into Group NC. Thus, using the Mahalanobis distance enables discrimination with the distance by taking variance between groups into account.

The Mahalanobis distance from each disease group thus calculated is converted into score S, which shows the possibility of belonging to each disease group, and the results of conversion are displayed in the display unit 14. Score S can be calculated, for example, using the following equation (6).

$$S = \frac{(1/D_{NC})}{(1/D_{NC}) + (1/D_S) + (1/D_D)} \times 100 \quad (6)$$

where $D_{NC}$, $D_S$ and $D_D$ show the Mahalanobis distance to Group NC, Group S and Group D, respectively.

Although the scores may be numerically displayed, they are preferably displayed graphically using, for example, a bar graph, which is understandable at a glance. FIG. 10 shows typical hemoglobin waveforms (FIG. 10 (a)) of normal subjects and schizophrenia and depressive patients, Mahalanobis distances to 3 disease groups (FIG. 10 (b)) regarding these waveforms obtained by the disease assessment apparatus 10 of this invention and the scores displayed in bar graph (FIG. 10 (c)). As illustrated in FIG. 10, according to the disease assessment apparatus 10, results of disease assessment are easy to be understood visually. The method for displaying these scores is not limited to the bar graph, if easy to understand visually. Reciprocal numbers of the Mahalanobis distance are used as scores here, but presence probability etc. can be also used.

The presence probability is a degree of attribution of a measurement data to each group expressed using 0-1, and can be calculated by the following equation (7), which is a modified equation (5) for finding a Mahalanobis distance.

$$g = \exp(-\sqrt{(C-m)\Sigma^{-1}(C-m)^t}) \quad (7)$$

Results of assessment are displayed as a subject's diagnosis report in the display unit 14, and can be printed as required. FIG. 11 shows an example of the report. The display column 111 at the top shows ID and name of the subject and date of examination, while the display column 112 in the middle shows measured waveforms to be displayed as reference (measured waveform of Ch21 in this report), a primary component waveform extracted by the primary component analysis, bar graphs for scores, findings and evaluation. The display column 113 in the bottom shows numerically or qualitatively the feature amount of each primary component waveform for oxygenated and de-oxygenated hemoglobin. It is preferable to store these diagnosis reports together with medical reports or medical interview reports containing other clinical data (including clinical diagnosis, medication, family history, organ disease, complications and other examinations), the measurement data for the subjects as shown in FIG. 8 and the image data obtained by the optical measurement. By doing so, a comprehensive medical history including the results of optical measurement for each patient can be produced, and the data can be read out and analyzed as required.

If the assessment results obtained by the disease assessment apparatus are identical with other diagnosis results, the results of feature analysis of the subject can be added to the database in the storage unit 12. These functions can be performed by receiving direction of selection of subjects and update of database on the main control unit of the disease assessment unit 10 from the input unit 13, for example, and by adding the results of feature analysis of said subject into the database. Such update can enlarge the size of the database and improve reliability of the assessment.

FIG. 12 shows an example of the main screen for disease assessment to be displayed in the display unit 4 of the disease assessment apparatus 10. In this case, operation buttons such as selective buttons 121 and 122 for selecting desired data (e.g. data of 4*4 channel and of 3*3), button 123 for calculating and displaying assessment, buttons 124 and 125 for storing and reading out assessment results, button 126 for producing new database or updating it, button 127 for producing a report and completion button 128 are displayed. By selecting either of these buttons by means of some inputting means, such as mouse, a series of operations including aforementioned calculation and display of assessment results, preparation of a report and updating of database are performed.

Results of assessment are stored by selecting the storing button 124, and can be readout by operating the readout button 125. New assessment results can be added to the database by operating the button 126.

As an embodiment of this invention, the disease assessment apparatus 10 that is independent from the biomedical optical apparatus 20 is explained above. It is also possible to integrate the disease assessment apparatus 10 of this invention with the optical measurement apparatus 20. In that case, the signal processing unit 31 can be equipped with the function of the operation unit 11 of the disease assessment apparatus 10. The functions of the storage unit 12, input unit 13 and operation unit 14 of the disease assessment apparatus 10 can be fulfilled by the input/output unit 32 and the storage unit 33 of the optical measurement apparatus 20.

Although above explanation is given with the examples of psychiatric disease cases, the disease assessment apparatus of this invention is applicable to other diseases than psychiatric disease.

BRIEF DESCRIPTION OF DRAWINGS

FIG. 3 is a diagram showing a feature waveform by each disease.

FIG. 5 is a diagram showing feature extraction in the disease assessment apparatus of this invention.

FIG. 6 is a table showing an example of database.

FIG. 10 is diagrams showing calculated Mahalanobis distances and examples of score display.

EXPLANATION OF SYMBOLS

Figure 1:
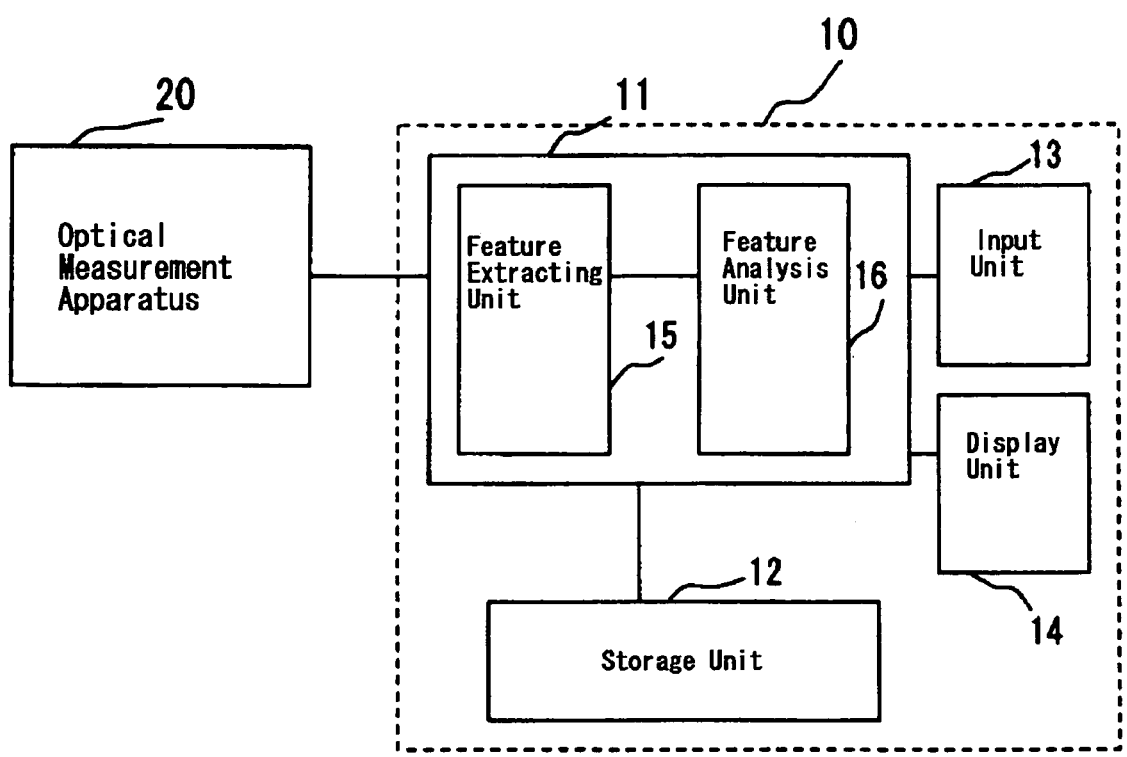
FIG. 1 is a block diagram showing an embodiment of the disease assessment apparatus of this invention.
Figure 2:
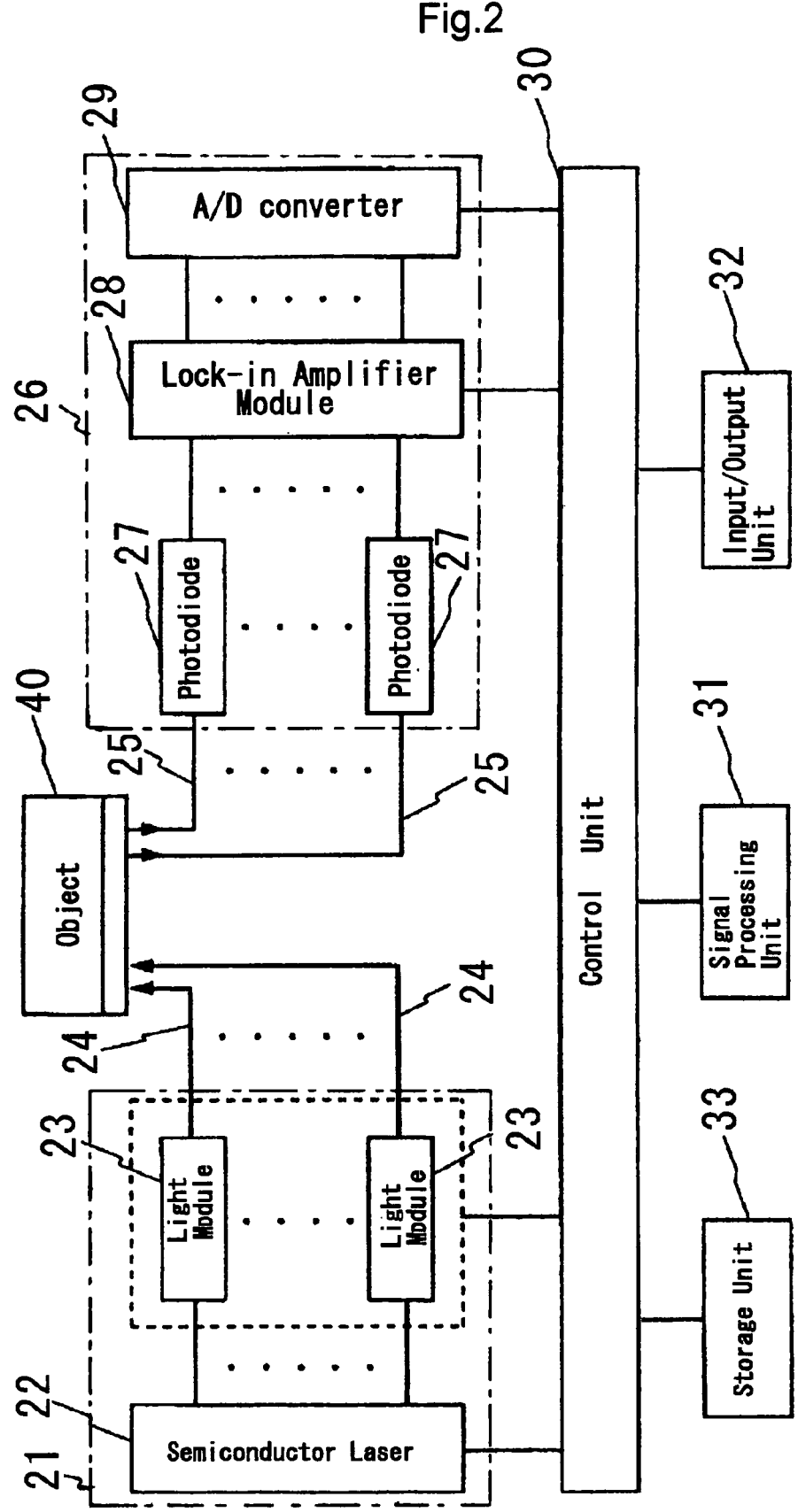
FIG. 2 is a block diagram showing an embodiment of the optical measurement apparatus of this invention.
Figure 4:
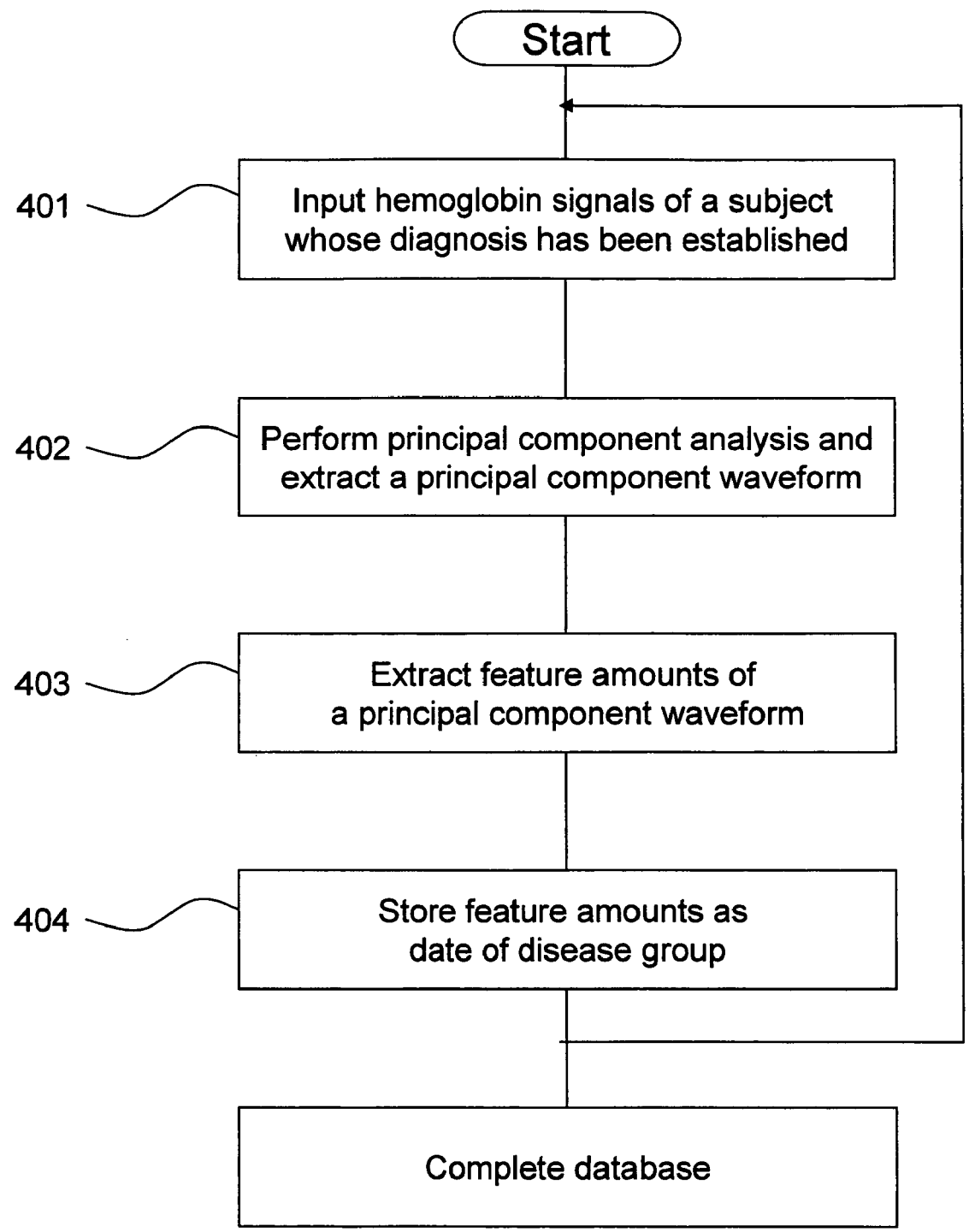
FIG. 4 is a diagram showing the procedures for preparing database in the disease assessment apparatus of this invention.
Figure 7:
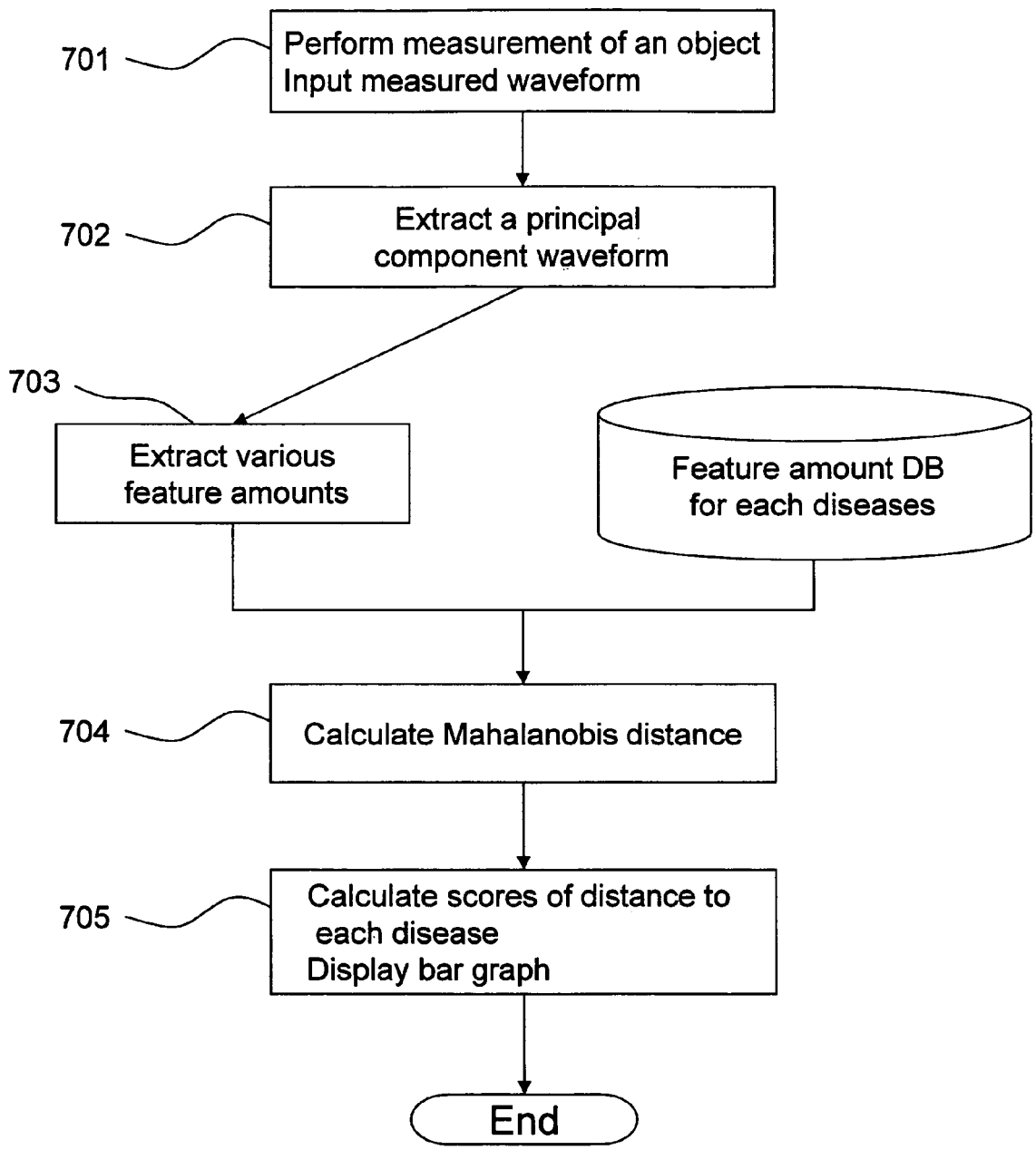
FIG. 7 is a diagram showing the procedures for assessing disease in the disease assessment apparatus of this invention.
Figure 8:
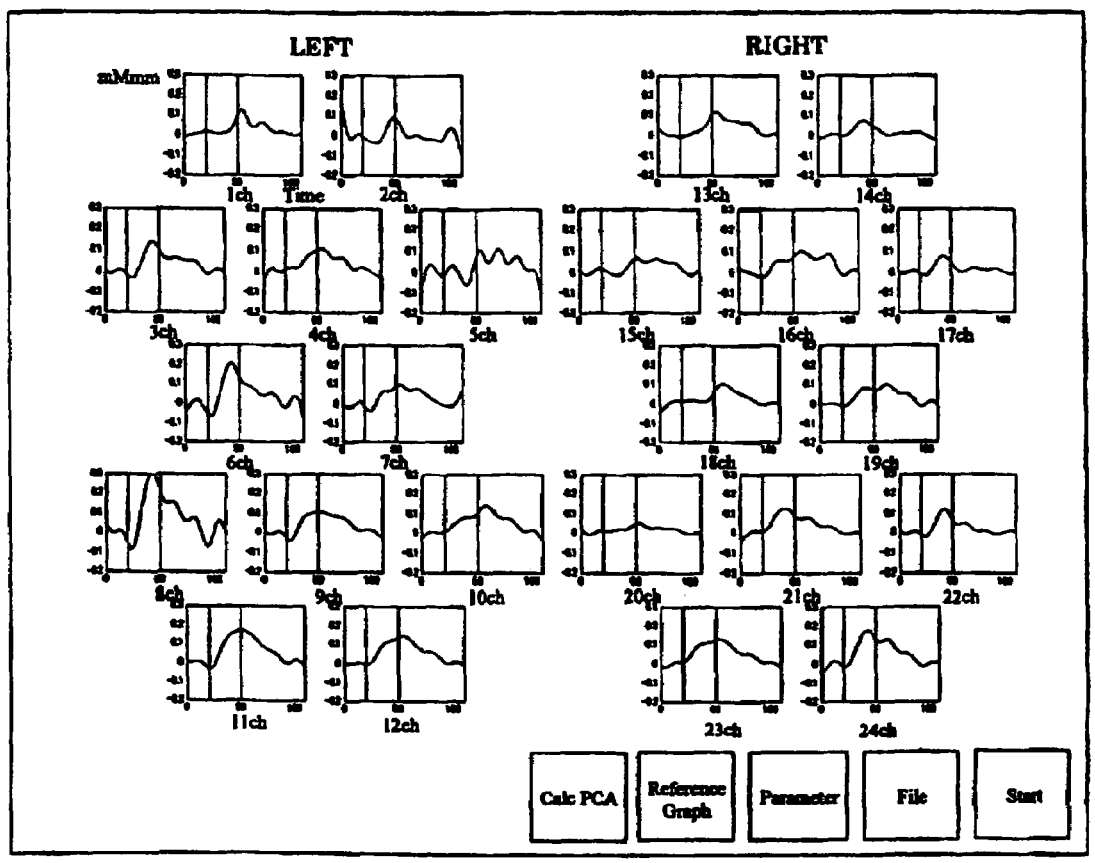
FIG. 8 is a diagram showing waveforms measured by the optical measurement.
Figure 9:
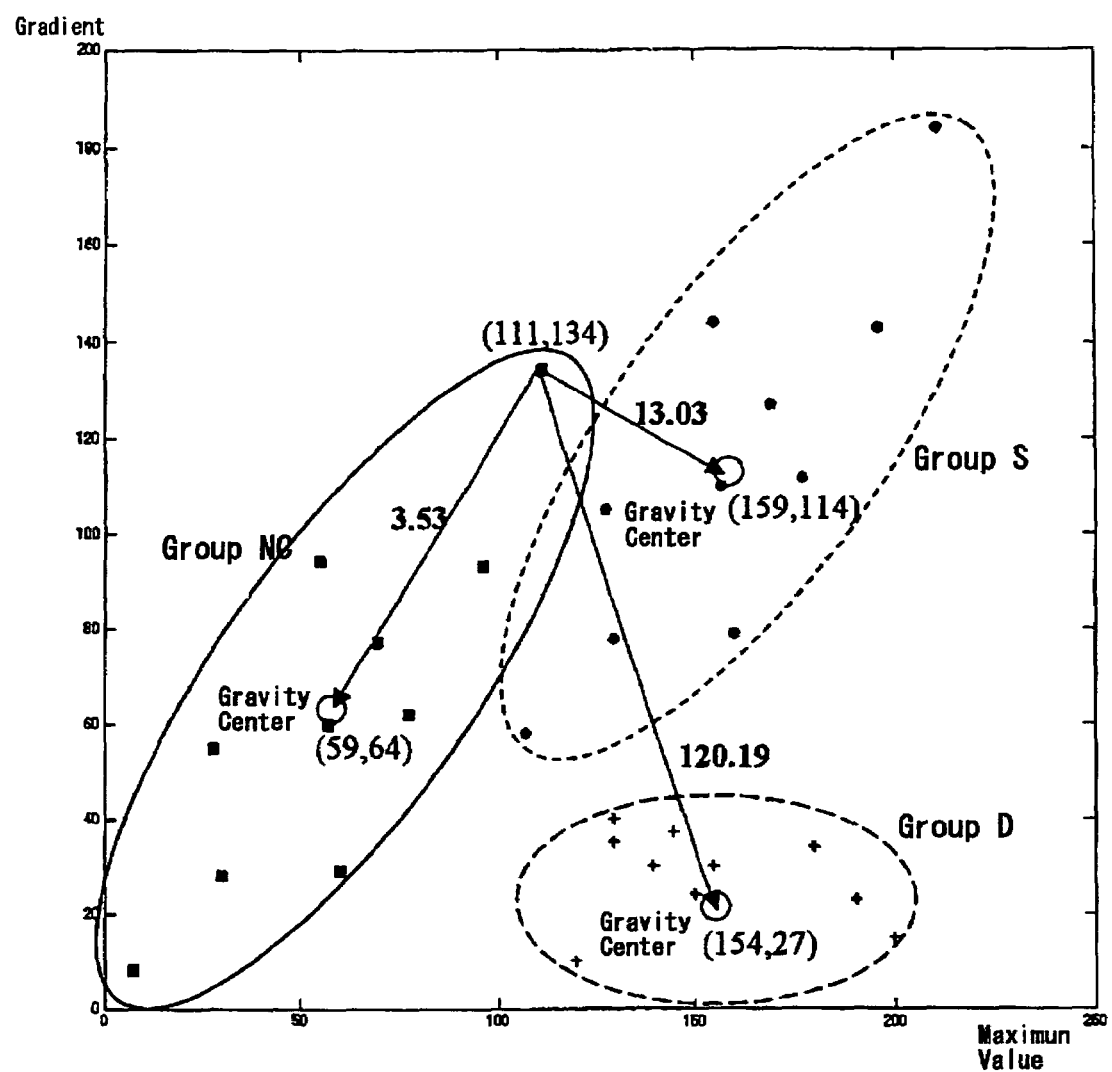
FIG. 9 is a diagram explaining Mahalanobis distance.
Figure 11:
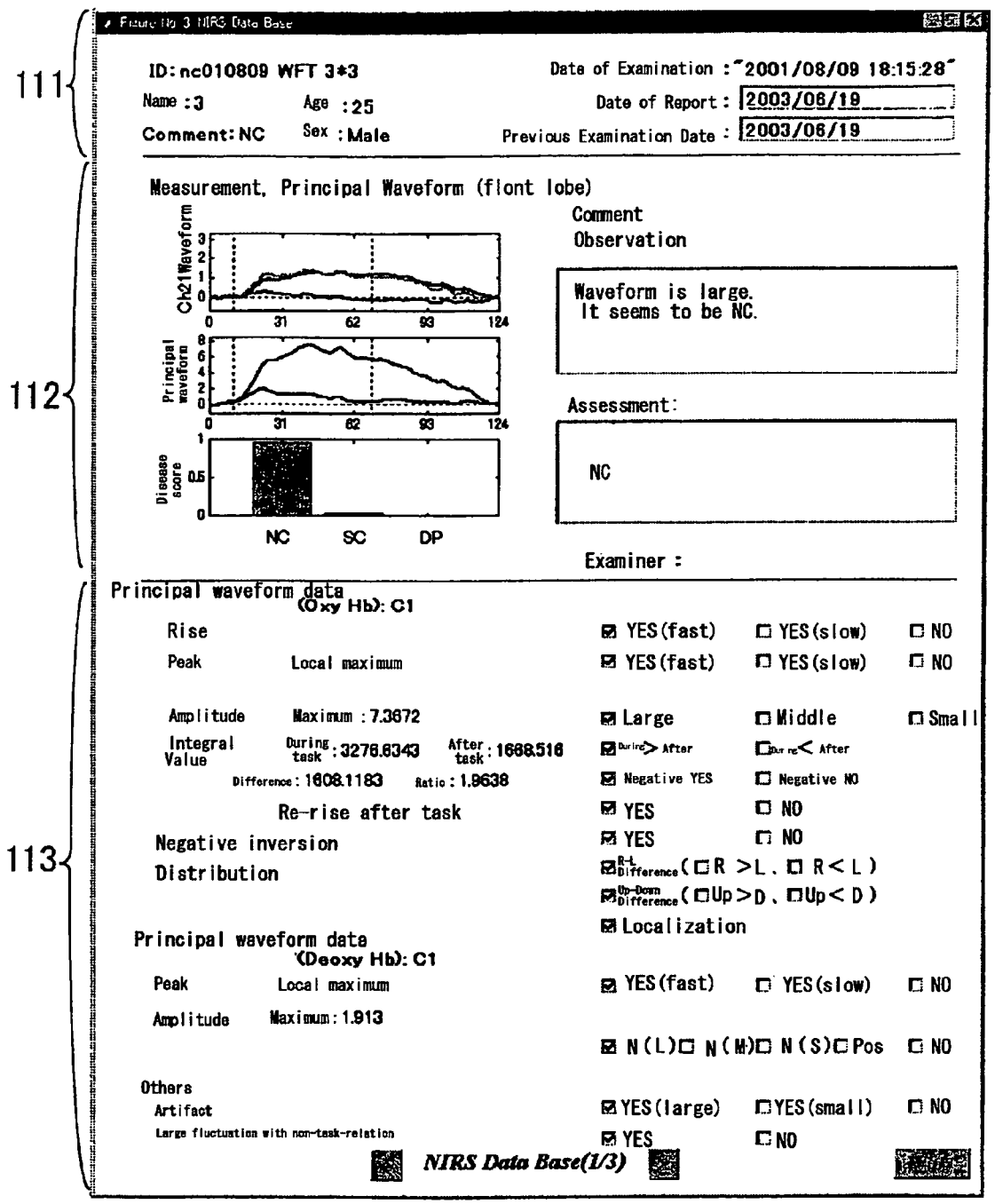
FIG. 11 is a diagram showing an example of assessment report produced by the disease assessment apparatus of this invention.
Figure 12:
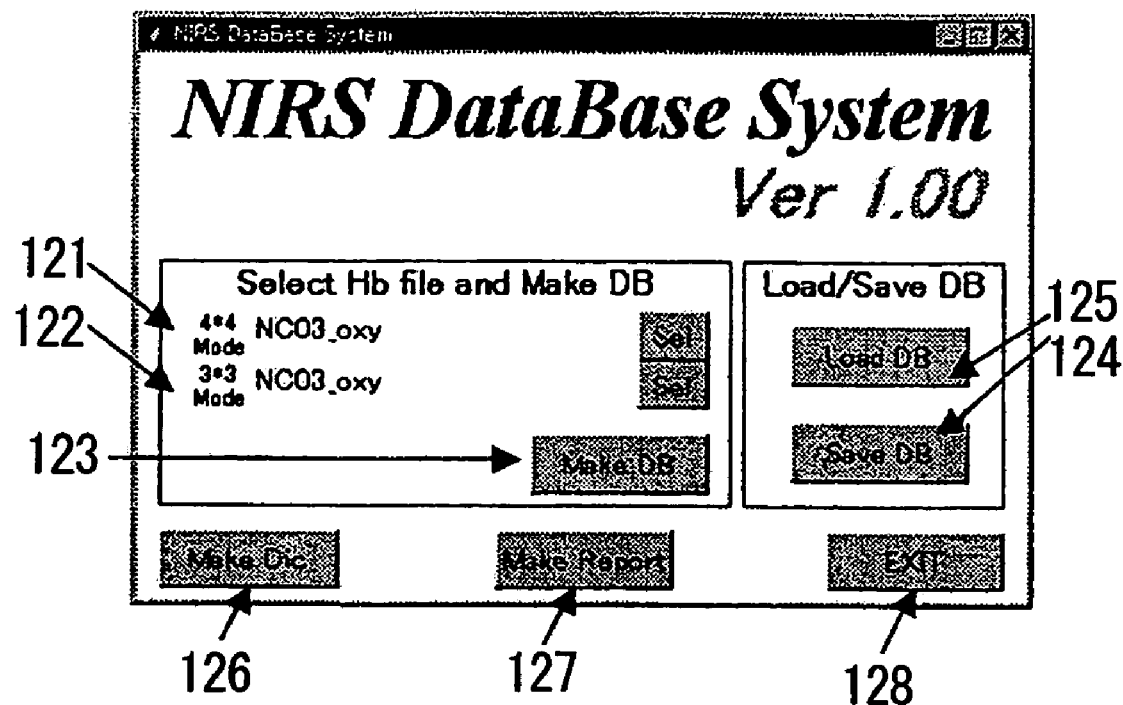
FIG. 12 is a diagram showing an example of operation scene of the disease assessment apparatus of this invention.

10 . . . disease assessment apparatus, 11 . . . operation unit, 12 . . . storage unit, 13 . . . input unit, 14 . . . display unit, 20 . . . optical measurement apparatus, 21 . . . light source unit, 22 . . . optical measurement unit, 30 . . . control unit.

The invention claimed is:

1. An optical measurement apparatus for a living body comprising a light source for generating a light to be irradiated onto an object to be examined, a light measurement means that detects a light transmitted inside the object and generates hemoglobin signals corresponding to hemoglobin changes in the object, an assessing means that analyzes feature amounts of the hemoglobin signals and assesses a disease of the object from the analyzed feature amount, and a display means for displaying disease information of the object, wherein said assessing means comprises:

an extracting means for extracting various kinds of feature amounts from the hemoglobin signals, a storing means for storing feature amounts of hemoglobin variation signals of multiple diseases in a database;

analyzing means for calculating a similarity of extracted feature amounts of an acquired hemoglobin variation signal with stored feature amounts of hemoglobin variation signals characterizing the multiple stored diseases in order to diagnose a disease of a subject; and a guantifying means for guantifying the similarity estimated by the analyzing means.

2. The optical measurement apparatus for a living body according to claim 1, wherein said display means displays said similarity in a graph.

3. The optical measurement apparatus for a living body according to claim 1, which further comprises a storing means that stores the assessed results for each subject together with its optical measurement data and image data as a combined data.

4. An optical measurement apparatus for a living body comprising a light source for generating a light to be irradiated onto an object to be examined, a light measurement means that detects a light transmitted inside the object and generates hemoglobin signals corresponding to hemoglobin changes in the object, an assessing means that analyzes feature amounts of the hemoglobin signals and assesses a disease of the object from the analyzed feature amount, and a display means for displaying disease information of the object, wherein said assessing means comprises:

an extracting means for extracting various kinds of feature amounts from the hemoglobin signals, a storing means for storing feature amounts of each of different disease types in a database, an analyzing means for analyzing feature amounts extracted by the extracting means and for estimating their similarity with the feature amounts of each disease stored in said storing means; and a quantifying means for quantifying the similarity estimated by the analyzing means.

5. The optical measurement apparatus for a living body according to claim 4, wherein said analyzing means calculates, by means of multivariate analysis, a similarity between various kinds of feature amounts extracted by said extracting means and the feature amounts of each disease stored as data in the storing means.

6. The optical measurement apparatus form living body according to claim 4, wherein said analyzing means calculates said similarity by calculating Mahalanobis distances between the feature amounts of the subject and the gravity center of the feature amount data of each disease.

7. The optical measurement apparatus for a living body according to claim 4, wherein said extracting means extracts the various kinds of feature amounts from a pattern (graph) of changes in the hemoglobin amount when a specified task is loaded onto the object.

8. The optical measurement apparatus for a living body according to claim 7, wherein said extracting means extracts, as said feature amounts, at least one of a gradient of the graph immediately after the initiation of a task, a gradient of the graph after the completion of the task, an integral value A during the task, an integral value B after the completion of the task, a ratio of the integral values (NB), a maximum value of the graph and a correlation value with square waveform after the completion of the task.

9. The optical measurement apparatus for a living body according to claim 4, wherein said extracting means uses an average of values obtained by multiple measurements as the hemoglobin signals.

10. The optical measurement apparatus for a living body according to claim 4, wherein said storing means includes a database of feature amounts for, at least, normal subject group, schizophrenia group and depression group.

11. The optical measurement apparatus for a living body of claim 4, wherein said analyzing means stores a data of a subject whose similarity with a particular disease is within a predetermined threshold, as a data of the particular disease.

12. The optical measurement apparatus for a living body according to claim 4, which further comprises an input means for inputting direction of assessment by the assessing means, preparation of reports, update of the database and displaying by the display means.

13. A method of assessing a disease of an object to be examined using hemoglobin signals of the object measured by optical measurement comprising the steps of:
    measuring hemoglobin signals by optical measurement for a plurality of subjects whose diagnosis of disease among a plurality of disease groups has been established,
    extracting a plurality of feature amounts from the hemoglobin signal of each subject,
    storing the feature amounts as data in a database,
    assessing disease of the object to be examined by extracting a plurality of feature amounts from a hemoglobin signal measured by optical measurement for the object to be examined, calculating a similarity of the extracted feature amounts with data for each disease, and
    determining a disease having a highest similarity as a disease of the object to be examined.

14. A method of assessing a disease according to claim 13, which further comprises the steps of extracting principal component waveform by performing principal component analysis for hemoglobin signals of a plurality of subjects each whose diagnosis of disease has been established, extracting feature amounts from the principal component waveform of each object, and storing the extracted feature amount as data of the disease of the object.

* * * * *